US012778775B2

(12) United States Patent
Lin et al.

(10) Patent No.: US 12,778,775 B2
(45) Date of Patent: Nov. 3, 2026

(54) BIODEGRADABLE DOUBLE-J STENT AND METHOD OF MANUFACTURING THE SAME

(71) Applicants: HORIEN BIOCHEMICAL TECHNOLOGY CO.,LTD., Taichung City (TW); ALAN VISION INVESTMENT CORPORATION, Taichung City (TW)

(72) Inventors: Ying-Chih Lin, Taichung City (TW); Yung-Chen Chang, Taichung City (TW)

(73) Assignees: HORIEN BIOCHEMICAL TECHNOLOGY CO., LTD., Taichung City (TW); ALAN VISION INVESTMENT CORPORATION, Taichung City (TW)

(*) Notice: Subject to any disclaimer, the term of this patent is extended or adjusted under 35 U.S.C. 154(b) by 0 days.

(21) Appl. No.: 18/444,629

(22) Filed: Feb. 17, 2024

(65) Prior Publication Data

US 2024/0299197 A1 Sep. 12, 2024

Related U.S. Application Data

(60) Provisional application No. 63/450,970, filed on Mar. 9, 2023.

(30) Foreign Application Priority Data

Sep. 21, 2023 (TW) ................................ 112136088

(51) Int. Cl.
*A61F 2/94* (2013.01)
*A61L 31/02* (2006.01)
(Continued)

(52) U.S. Cl.
CPC .............. *A61F 2/94* (2013.01); *A61L 31/022* (2013.01); *A61L 31/044* (2013.01); *A61L 31/10* (2013.01);
(Continued)

(58) Field of Classification Search
CPC ............................. A61F 2/94; A61F 2250/003
See application file for complete search history.

(56) References Cited

U.S. PATENT DOCUMENTS 6,368,356 B1 * 4/2002 Zhong ................. A61M 27/008 523/105
8,414,656 B2 * 4/2013 Davoudi ........... A61M 25/0043 623/23.7
(Continued)

FOREIGN PATENT DOCUMENTS

CN 102579171 A 7/2012
CN 104473706 A 4/2015
(Continued)

OTHER PUBLICATIONS

Taiwan Application Serial No. 112136088, Office Action mailed May 14, 2024 and its translation.
(Continued)

*Primary Examiner* — Philip R Wiest
*Assistant Examiner* — Peter Daniel Smith
(74) *Attorney, Agent, or Firm* — Winston Hsu

(57) ABSTRACT

A biodegradable double-J stent and a method of manufacturing a biodegradable double-J stent are provided. The stent comprises a main tube, a first retaining tube, and a second retaining tube, each fabricated from a biodegradable material. The first and second retaining tubes are curl-shaped and are connected to two ends of the main tube, respectively. The method of manufacturing a biodegradable double-J stent comprises the steps of: (a) providing a tube made of a
(Continued)

2 biodegradable material; and (b) bending two ends of the tube to render the two ends curl-shaped and keeping a middle segment between the two ends straight. The two curl-shaped ends define a first retaining tube and a second retaining tube, respectively, and the middle segment defines a main tube. The biodegradable double-J stent precludes a ureteral obstruction which might otherwise occur with conventional double-J stents not removed in a timely manner.

20 Claims, 11 Drawing Sheets

(51) Int. Cl.
*A61L 31/04* (2006.01)
*A61L 31/10* (2006.01)

(52) U.S. Cl.
CPC ................. *A61F 2210/0004* (2013.01); *A61F 2210/0009* (2013.01); *A61F 2230/0041* (2013.01); *A61F 2230/0091* (2013.01); *A61F 2240/001* (2013.01); *A61F 2250/003* (2013.01)

(56) References Cited

U.S. PATENT DOCUMENTS 11,213,414 B2 * 1/2022 DeGraaf ................... A61F 2/91
2006/0147501 A1 * 7/2006 Hillas ..................... A61L 27/24 424/443
2007/0014831 A1 1/2007 Sung
2008/0004578 A1 * 1/2008 Hixon ..................... A61L 31/16 604/326
2011/0153000 A1 6/2011 Schwartz
2015/0005893 A1 1/2015 Harrah
2016/0015509 A1 1/2016 McDonough
2020/0246505 A1 * 8/2020 Francis ................... A61L 17/14
2022/0071756 A1 * 3/2022 Cartledge ................. A61F 2/04
2022/0079785 A1 3/2022 DeGraaf

FOREIGN PATENT DOCUMENTS

CN 112915265 6/2021
CN 112915265 A 6/2021
WO 00/50103 8/2000
WO 00/50103 A1 8/2000

OTHER PUBLICATIONS

Taiwan Application Serial No. 112136088, Claims in Response filed Jun. 3, 2024 to Office action mailed May 14, 2024 and its translation.

Taiwan Application Serial No. 112136088, Notice of Allowance mailed Sep. 24, 2024 and its translation.

* cited by examiner

2

3

4

0 minute after being stretched 5 minutes after being stretched

BIODEGRADABLE DOUBLE-J STENT AND METHOD OF MANUFACTURING THE SAME

CROSS-REFERENCE TO RELATED APPLICATION

This non-provisional application claims priority under 35 U.S.C. § 119 (a) on Patent Application No(s). 112136088 filed in Taiwan, R.O.C. on Sep. 21, 2023, the entire contents of which are hereby incorporated by reference.

This non-provisional application claims priority under 35 U.S.C. § 119 (e) on U.S. provisional Patent Application No(s). 63/450,970 filed on Mar. 9, 2023, the entire contents of which are hereby incorporated by reference.

BACKGROUND OF THE INVENTION

1. Field of the Invention

The present disclosure relates to a double-J stent, and a method of manufacturing the double-J stent, and in particular to a biodegradable double-J stent.

2. Description of the Related Art

A double-J stent (also known as Double-J), often used by urologic surgeons to treat patients, has J-shaped curls at both ends. The double-J stent is a thin, flexible plastic tube that is temporarily in a patient's ureter to help urine pass from an affected kidney into the urinary bladder with a view to helping the patient avoid suffering from hydronephrosis which might otherwise be caused by a ureteral stricture or obstruction. The J-shaped structures at the two ends of the double-J stent are attached to the patient's urinary bladder and affected kidney, respectively.

In general, a double-J stent that has been placed in a patient's ureter for 1.5 months to 6 months has to be changed or removed to prevent encrustation and kidney stone formation which may otherwise occur as a result of leaving the stent indwelling too long. The encrustation and kidney stone formation in the double-J stent leads to urinary tract obstruction and the resultant retention of urine in the affected kidney.

BRIEF SUMMARY OF THE INVENTION

In clinical practice, it is not uncommon for double-J stents placed in ureters to be forgotten and thus not removed in a timely manner. The overstaying double-J stents are predisposed to encrustation and kidney stone formation which in turn causes a ureteral obstruction and resultant severe problems, such as hydronephrosis and renal failure. Therefore, it is imperative to prevent double-J stents placed in ureters from being forgotten and ensure their timely removal.

In view of the aforesaid drawbacks of the prior art, it is an objective of the present disclosure to provide a biodegradable double-J stent comprising: a main tube made of a biodegradable material with biocompatibility and having a first end portion and a second end portion opposing the first end portion; a first retaining tube made of the biodegradable material, curled, and connected to the first end portion of the main tube; and a second retaining tube made of the biodegradable material, curled, and connected to the second end portion of the main tube.

In an embodiment of the present application, the biodegradable material for double-J stent is selected from either extracellular matrix-derived material or pure collagen.

In an embodiment of the present application the biodegradable double-J stent, the main tube, and/or the first retaining tube features a first degradation rate, and the second retaining tube features a second degradation rate, with the first and second degradation rates being different from each other.

In an embodiment of the present application the biodegradable double-J stent, the first degradation rate is faster than the second degradation rate.

In an embodiment of the present application the biodegradable double-J stent, the first degradation rate is slower than the second degradation rate.

The biodegradable double-J stent further comprises a lubrication layer made of a biocompatible, hydrophilic material, or has a surface hydrophilically modified, wherein the lubrication layer is coated on: (i) the main tube, the first retaining tube, and the second retaining tube; or (ii) the main tube and the first retaining tube.

In an embodiment of the present application the biodegradable double-J stent, the lubrication layer is 1 μm to 0.66 mm in thickness.

The biodegradable double-J stent is further coated with a contrast agent made of a biocompatible radiopaque material, wherein the contrast agent is coated on: (i) the main tube, the first retaining tube, and the second retaining tube; or (ii) at least one of the first retaining tube and the second retaining tube.

In an embodiment of the present application the biodegradable double-J stent, the contrast agent layer is 1 μm to 0.66 mm in thickness.

The biodegradable double-J stent further comprises a contrast agent and lubrication combo layer made of a mixture of a biocompatible radiopaque material and a biocompatible, hydrophilic material, wherein the contrast agent and lubrication combo layer is coated on: (i) the main tube, the first retaining tube, and the second retaining tube; or (ii) at least one of the first retaining tube and the second retaining tube.

In an embodiment of the present application the biodegradable double-J stent, the contrast agent and lubrication combo layer is 1 μm to 0.66 mm in thickness.

In an embodiment of the present application the biodegradable double-J stent, the main tube, the first retaining tube, and the second retaining tube are integrally formed.

In an embodiment of the present application the biodegradable double-J stent, the main tube, the first retaining tube, and the second retaining tube each have a helical structure comprising a helical body curling and winding along an axis, and the helical structure comprises a plurality of helical circles spaced apart from each other by a pitch of 0 mm to 2.5 mm.

In an embodiment of the present application the biodegradable double-J stent, the helical body is a plate.

In an embodiment of the present application the biodegradable double-J stent, the helical body is a screw rod.

In an embodiment of the present application the biodegradable double-J stent, the wall of the main tube is 10 μm to 3.3 mm in thickness.

In an embodiment of the present application the biodegradable double-J stent, the main tube has an outer diameter of 0.33 mm to 3.33 mm.

To achieve the above and other objectives, the present disclosure provides a method of manufacturing a biodegradable double-J stent, comprising the steps of:

(a) providing a tube made of a biodegradable material with biocompatibility; and (b) bending two ends of the tube to render the two ends curl-shaped and keeping a middle segment between the two ends straight, wherein the two curl-shaped ends define a first retaining tube and a second retaining tube, respectively, and the middle segment defines a main tube.

In an embodiment of the present application the biodegradable material is selected from either extracellular matrix-derived material or pure collagen.

In an embodiment of the present application the tube is a helical tube.

In an embodiment of the present application the helical tube is made by winding a plate on a core.

In an embodiment of the present application the helical tube is made by winding a screw rod on a core.

In an embodiment of the present application the core is made of Teflon or stainless steel.

In an embodiment of the present application the core has a diameter ranging from 0.9 mm to 3.3 mm.

In an embodiment of the present application the main tube and the first retaining tube undergo a crosslinking process, and the main tube and/or the first retaining tube features a higher degradation rate than the second retaining tube or a lower degradation rate than the second retaining tube because of the crosslinking process.

In an embodiment of the present application the crosslinking process is carried out with a crosslinking agent being one selected from the group consisting of an aldehyde-based crosslinking agent, isocyanate-based crosslinking agent, acyl azide-based crosslinking agent, epoxide-based crosslinking agent, quinone-based crosslinking agent, carbohydrate-based crosslinking agent, polyphenol-based crosslinking agent, and iridoid glycoside-based crosslinking agent.

In an embodiment of the present application the crosslinking agent is carbodiimide/N-hydroxysuccinimide crosslinking agent.

In an embodiment of the present application the second retaining tube undergoes a deamidation process.

The biodegradable double-J stent and the method of manufacturing a biodegradable double-J stent are effective in preventing ureteral obstruction which might otherwise occur with conventional double-J stents not removed in a timely manner.

DETAILED DESCRIPTION OF THE INVENTION

To facilitate understanding of the objectives, characteristics, and effects of the present disclosure, embodiments together with the attached drawings for the detailed description of the present disclosure are provided.

In an embodiment of the present disclosure the method of manufacturing a biodegradable double-J stent comprised the following.

First, provide a biodegradable material. In an embodiment of the present disclosure, the biodegradable material is collagen. In an embodiment of the present disclosure, the biodegradable material is a biocompatible biodegradable material, such as starch, polylactic acid, and a natural material derived from an organism. In an embodiment of the present disclosure, the biodegradable material is plate-shaped in its initial state. In an embodiment of the present disclosure, the biodegradable material can be filament-shaped, powder-shaped, block-shaped, or of any other shapes in its initial state, provided that it is feasible to further process the biodegradable material.

Then, the biodegradable material is processed to take on a slender, tubular shape and cured by being dried with hot air current, so as to obtain the tube required for subsequent processing. In a variant manufacturing process, the preferred curing technique incudes physical curing and chemical curing. The physical curing is carried out with, for example, hot air drying, freeze drying, vacuum dehydration, UV, or microwave. The chemical curing is carried out with, for example, ionic crosslinking, chemical bond-based crosslinking, or enzymatic crosslinking.

Next, the two ends of the tube are pressed into a pigtail-shaped mold to bend the two ends of the tube and allow the two ends to become curl-shaped, allowing the two curl-shaped ends of the tube to function as the retaining ends of the double-J stent. Thus, the two ends of the double-J stent are attached to the patient's urinary bladder and affected kidney, respectively. The middle segment between the two ends of the tube is kept straight to function as the main tube for guiding the urine out of the human body. At this point in time, the manufacturing of a biodegradable double-J stent is finished. In a variant manufacturing process, the two ends of the tube are bent with, for example, a pair of pliers and the like, to allow the two ends to become curl-shaped.

Figure 1:
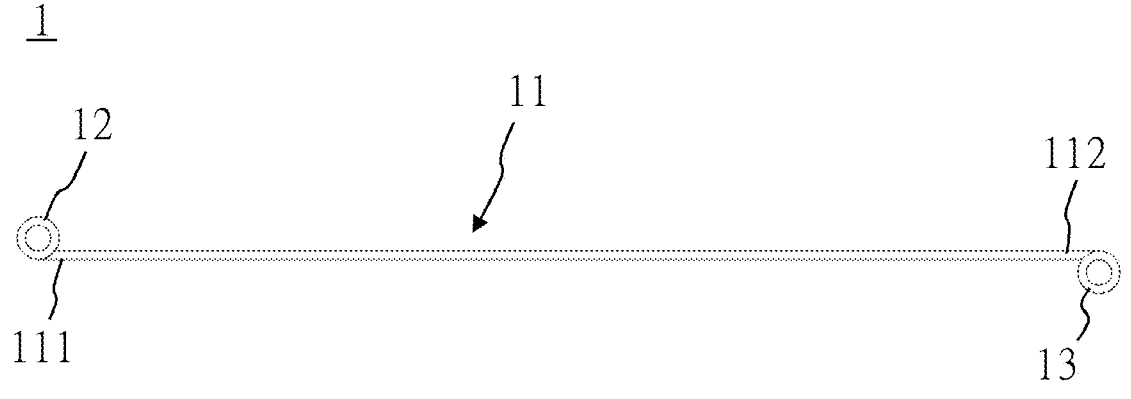
FIG. 1 is a schematic perspective view of a biodegradable double-J stent according to an embodiment of the present disclosure.

A biodegradable double-J stent 1 in an embodiment of the present disclosure is shown in FIG. 1. The biodegradable double-J stent 1 comprises a main tube 11, a first retaining tube 12, and a second retaining tube 13. The main tube has a first end portion 111 and a second end portion 112 opposing the first end portion 111. The first retaining tube 12 is curl-shaped and is connected to the first end portion 111 of the main tube 11. The second retaining tube 13 is curl-shaped and is connected to the second end portion 112 of the main tube 11. In an embodiment of the present disclosure, the biodegradable double-J stent 1 undergoes the aforesaid processing so as to be integrally formed. The main tube 11 is the middle segment of the tube during the double-J stent manufacturing process. The first retaining tube 12 and the second retaining tube 13 are the two ends of the tube during the double-J stent manufacturing process, respectively. In a variant manufacturing process, the biodegradable double-J stent 1 need not be integrally formed, provided that the first retaining tube 12 is connected to the first end portion 111 of the main tube, and the second retaining tube 13 to the second end portion 112 of the main tube 11. Therefore, the manufacturing of the biodegradable double-J stent of the present disclosure is not restricted.

In an embodiment of the present disclosure, the first retaining tube 12 and the second retaining tube 13 are merely intended to be illustrative of two retaining parts of the biodegradable double-J stent 1 but not intended to specify any specific retaining parts. For example, when the biodegradable double-J stent 1 is in an upright state, the first retaining tube 12 is an upper retaining part or a lower retaining part of the biodegradable double-J stent 1, and the second retaining tube 13 is another retaining part of the biodegradable double-J stent 1.

The material of which the biodegradable double-J stent 1 is made is a biodegradable material with biocompatibility. Even if the biodegradable double-J stent 1 is placed in a patient's ureter but is not removed in a timely manner afterward, the biodegradable double-J stent 1 inside the patient's body can still degrade spontaneously. In the course of the degradation, the biodegradable double-J stent 1 undergoes a gradual reduction in mechanical strength and thickness and eventually turns into soft, thin-film-shaped or thin-yarn-shaped collagen material. Therefore, the biodegradable double-J stent 1 in an embodiment of the present disclosure precludes a ureteral obstruction which might otherwise occur with conventional double-J stents not removed in a timely manner.

In an embodiment of the present disclosure the method of manufacturing a biodegradable double-J stent comprises the following.

First, provide a biodegradable material. In an embodiment of the present disclosure, the biodegradable material is extracellular matrix derived from porcine small intestine. The extracellular matrix-derived material is plate-shaped. Please refer to Taiwan patent I533560 for a method of preparing the extracellular matrix-derived material. The extracellular matrix-derived material is cut to form a slender plate 10 mm in width and 1,200 mm in length.

Then, prepare a core. The core used in an embodiment of the present disclosure is a Teflon cord. In a variant manufacturing process, the core is made of stainless steel or any other materials with appropriately low surface roughness and low surface energy. With the core exhibiting the aforesaid properties, the extracellular matrix-derived material winds easily on the core. The core has a diameter of 1.09 mm. The diameter of the core is adjustable within the range of 0.9 mm to 3.3 mm, depending on the requirements of the manufacturing process of the double-J stent. For example, the wider the channel in the double-J stent is, the greater the core diameter is, and vice versa. The lower end of the extracellular matrix-derived material is fixed to the surface of the core, and the extracellular matrix-derived material winds around the core clockwise (or counterclockwise) and upward while tilting relative to the axis of the core by a tilt angle of less than 45° (or at least less than) 90° so as for the extracellular matrix-derived material to take on a helical structure. At this point in time, the extracellular matrix-derived material functions as a helical body of the helical structure. After winding completely around the core, the extracellular matrix-derived material fully takes on the helical structure. The helical structure comprises a plurality of helical circles spaced apart from each other by a pitch of around 0.5 mm. The pitch of the helical structure is adjustable within the range of 0 mm to 2.5 mm, depending on the manufacturing process of and application needs for the double-J stent.

The thickness of the wall of the main tube is 100 μm and is adjustable within the range of 10 μm to 3.3 mm. The outer diameter of the main tube is 1.98 mm and is adjustable within the range of 0.33 mm to 3.33 mm. The aforesaid dimensions of the wall thickness and outer diameter enable the main tube to manifest high mechanical strength and excellent applicability. However, in a variant embodiment, the dimensions of the wall thickness and outer diameter of the main tube are subject to changes as needed.

Figure 2:
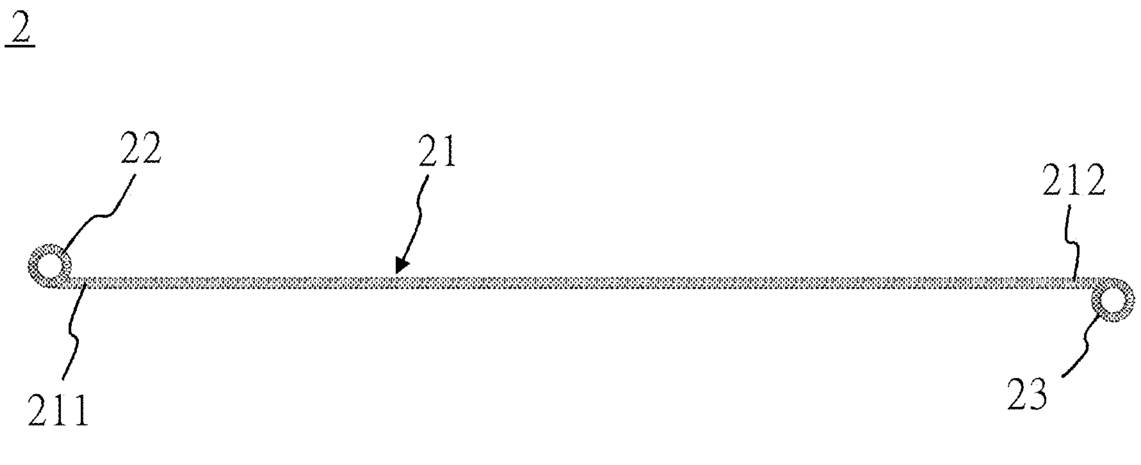
FIG. 2 is a perspective view of a biodegradable double-J stent according to an embodiment of the present disclosure.
Figure 3:
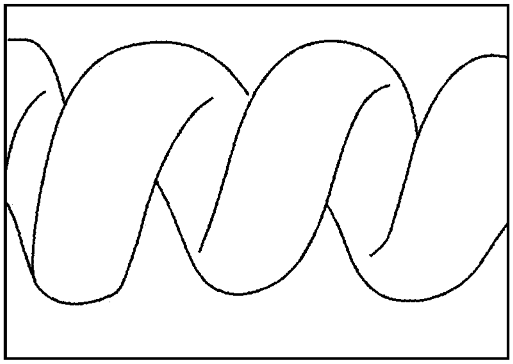
FIG. 3 is a partial enlarged view of the biodegradable double-J stent according to an embodiment of the present disclosure.

Then, the two ends of the helical structure are bent to become curl-shaped with the method in an embodiment of the present disclosure. Next, the bent helical structure undergoes a drying process with air at room temperature. In an embodiment of the present disclosure after the bent helical structure has dried with air, it is removed from the core to obtain a biodegradable double-J stent 2. The biodegradable double-J stent 2 in an embodiment is shown in FIG. 2 and FIG. 3, and its overall appearance therein is substantially the same as the biodegradable double-J stent 1 in a previous embodiment except for the helical structures of the biodegradable double-J stent 2.

In an embodiment of the present disclosure the biodegradable double-J stent 2 is made of an extracellular matrix-derived material derived from a decellularized organism and thus is biocompatible. By processing the extracellular matrix-derived material into a helical structure, the inherent structural strength, intrinsically lower than that of synthetic biodegradable materials, is enhanced. After the biodegradable double-J stent 2 has been placed in a patient's body, it degrades by at least 95% by around the $12^{th}$ week. The timing may fall within the range from the $11^{th}$ week to the $13^{th}$ week, depending on the internal environment of the patient's body. However, the main tube 21, the first retaining tube 22, and the second retaining tube 23 of the biodegradable double-J stent 2 are separately processed to adjust the degradation rate of the main tube 21, the first retaining tube 22, and the second retaining tube 23, allowing the main tube 21, the first retaining tube 22, and the second retaining tube 23 to have different degradation rates.

In an embodiment of the present disclosure the method of manufacturing a biodegradable double-J stent comprises the following.

In an embodiment of the present disclosure a biodegradable double-J stent 3 is obtained by further performing a degradation rate process on the biodegradable double-J stent 2 such that a main tube 31 and a first retaining tube 32 of the biodegradable double-J stent 3 degrade faster than a second retaining tube 33 of the biodegradable double-J stent 3.

The process flow of manufacturing the biodegradable double-J stent of an embodiment is described below.

A biodegradable double-J stent finished product is manufactured with the method of manufacturing a biodegradable double-J stent previously described. However, the biodegradable double-J stent finished product remains wound on the core and waits for further processing. The degradation rate of the processing parts mentioned below is adjusted.

Then, the main tube processing part and the first retaining tube processing part of the biodegradable double-J stent finished product are soaked in a sodium hydroxide solution with a concentration of 0.6N for 12 hours to undergo a deamidation process. After that, the main tube processing part and the first retaining tube processing part undergo rinsing and neutralization of the deamidation reaction to finalize the deamidation process. Next, the second retaining tube processing part of the biodegradable double-J stent finished product undergoes a crosslinking process. In an embodiment of the present disclosure, a solution (using water or PBS as the solvent) of a mixture of 14 mM of carbodiimide and 5.5 mM of N-hydroxysuccinimide functions as a crosslinking agent for carrying out a chemical crosslinking process. The crosslinking process entails soaking the second retaining tube processing part in the crosslinking agent for 12 hours to undergo a crosslinking reaction, removing the second retaining tube processing part from the crosslinking agent after the second retaining tube processing part has undergone the crosslinking reaction for 12 hours, and rinsing the second retaining tube processing part with pure water to stop the crosslinking reaction. Upon completion of the deamidation process and the crosslinking reaction, the biodegradable double-J stent 3 is obtained.

In a variant manufacturing process, the crosslinking process is carried out by physical crosslinking. An exemplary manufacturing process based on physical crosslinking requires dehydrothermal crosslinking and UV crosslinking. The dehydrothermal crosslinking entails heating up the second retaining tube processing part to around 85~105° C. under a vacuum degree of less than 50 mTorr for 1~72 hours. The UV crosslinking entails performing UV irradiation on the second retaining tube processing part with the intensity ranging from 0.55 $W/cm^2$~5.5 $W/cm^2$ for 0.5 to 8 hours.

Figure 4:
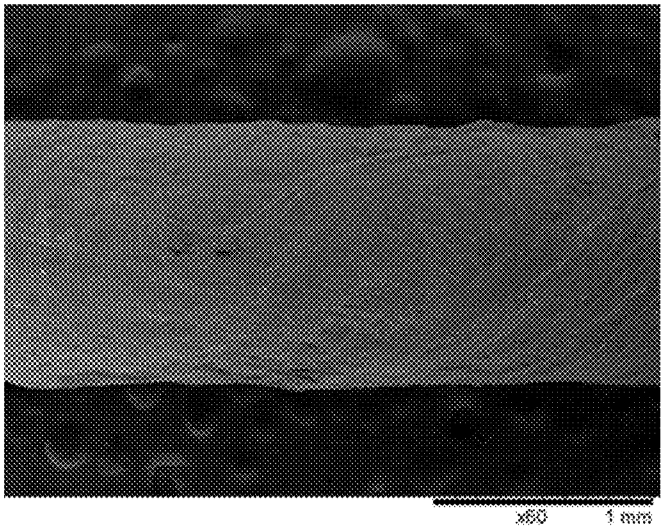
FIG. 4 is a partial enlarged view of a biodegradable double-J stent according to an embodiment of the present disclosure.

In an embodiment of the present disclosure the image taken of the biodegradable double-J stent 3 with an electron microscope (Hitachi TM1000) is shown in FIG. 4 and reveals a helical structure. To evaluate the degradation rate variations arising from the deamidation process and the crosslinking reaction that the biodegradable double-J stent 3 has undergone, a degradation simulation test is carried out and described below.

In an embodiment of the present disclosure degradation simulation test for the biodegradable double-J stent 3 comprises the following.

First, prepare the biodegradable double-J stent 3 and soak the biodegradable double-J stent 3 in 30 ml of 0.15 mg/ml protease K solution (using phosphate buffered saline as the solvent). The protease K solution is contained in a beaker. Then, the beaker which contains the protease K solution and the biodegradable double-J stent 3 is placed in a 37° C. incubator and shaken continuously at a rotation speed of 100 rpm for 7 days to simulate the implantation of the biodegradable double-J stent 3 in the internal environment of the human body.

Next, pictures are taken of the biodegradable double-J stent 3 immediately before being placed in the incubator and at hour 1, hour 4, hour 8, day 1, day 3, day 5 and day 7 after being placed in the incubator to observe the extent of the degradation of the biodegradable double-J stent 3.

Figure 5:
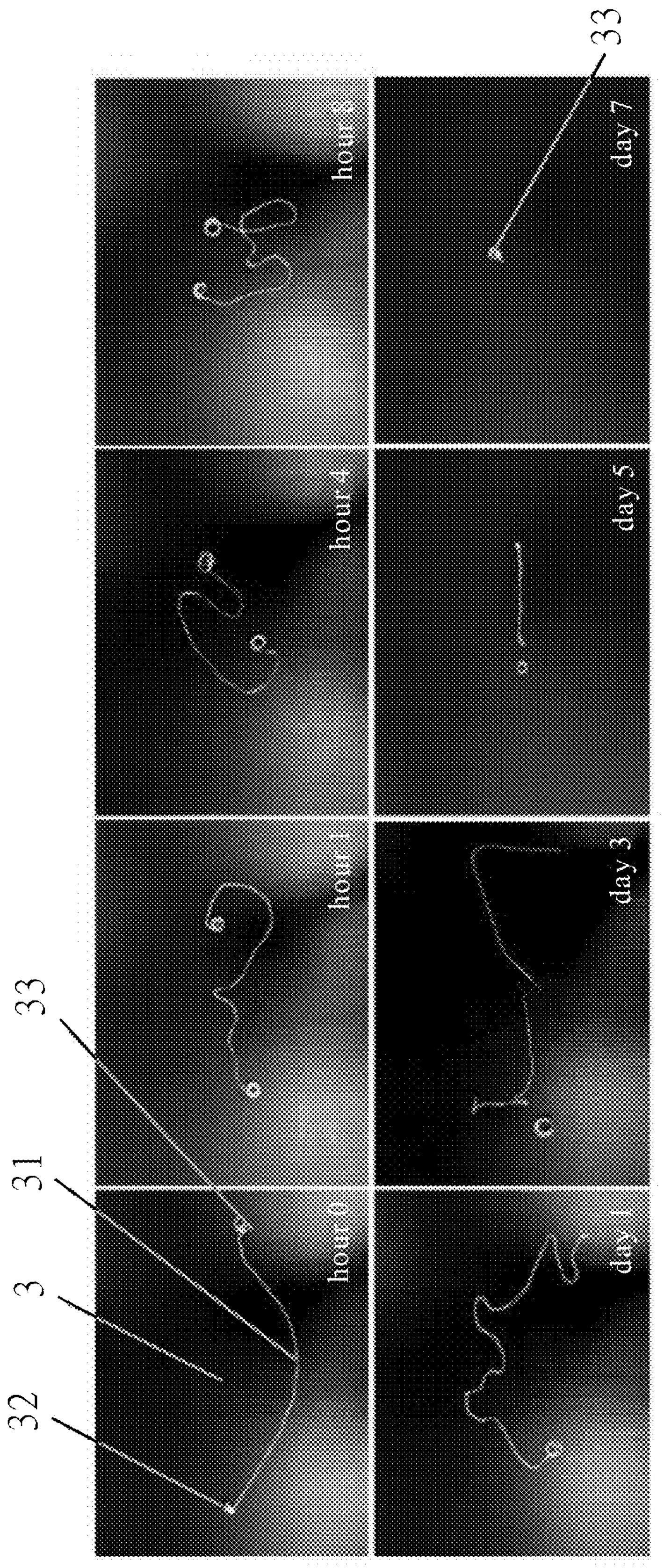
FIG. 5 shows a degradation simulation test result about the biodegradable double-J stent according to an embodiment of the present disclosure.

The degradation simulation test result is shown in FIG. 5. After undergoing the deamidation process, the main tube 31 and the first retaining tube 32 of the biodegradable double-J stent 3 have fully degraded. However, the second retaining tube 33 of the biodegradable double-J stent 3 undergoes the crosslinking process only and thus has not yet degraded. The main tube 31 and the first retaining tube 32 which have undergone the deamidation process have a first degradation rate. The degradation begins from the degradation simulation test (simulating the implantation of the biodegradable double-J stent 3 in the internal environment of the human body) and proceeds at the first degradation rate to attain degradation of at least 95% (100%, i.e., full degradation, in the degradation simulation test) by the end of the $7^{th}$ day. The second retaining tube 33 which has undergone the crosslinking process has a second degradation rate. The degradation initiates with the degradation simulation test and continues at the second degradation rate, yet remains incomplete as of the conclusion of the $7^{th}$ day. Therefore, the first degradation rate is faster than the second degradation rate.

In an embodiment of the present disclosure, the biodegradable double-J stent 3 is an acceleration-style stent with a degradation rate designed to meet clinical needs. For example, when the patient's urinary bladder is overly sensitive, the first retaining tube 32 fixed to the urinary bladder and the main tube 31 of the biodegradable double-J stent 3 is designed to have a faster degradation rate (i.e., the first degradation rate) and the second retaining tube 33 fixed to the affected kidney is designed to have a slower degradation rate (i.e., the second degradation rate). However, in a variant embodiment, the first degradation rate is designed to be slower than the second degradation rate to meet clinical needs, and the biodegradable double-J stent 3 is regarded as an extension-style biodegradable double-J stent. Furthermore, the biodegradable double-J stent 3 is designed to allow the main tube, the first retaining tube, and the second retaining tube to have equal degradation rate, and the degradation rate is acceleration-style, general-style, or extension-style.

In an embodiment of the present disclosure, the crosslinking agent is carbodiimide/N-hydroxysuccinimide. However, in other manufacturing processes, the crosslinking agent is one selected from the group consisting of an aldehyde-based crosslinking agent, isocyanate-based crosslinking agent, acyl azide-based crosslinking agent, epoxide-based crosslinking agent, quinone-based crosslinking agent, carbohydrate-based crosslinking agent, and polyphenol-based crosslinking agent.

In an embodiment of the present disclosure, the deamidation process is carried out with sodium hydroxide solution. However, in a variant manufacturing process, the deamidation process is carried out with an alkaline solution, such as lime-sodium sulfide solution, and 3-(cyclohexylamino)-1-propanesulphonic acid (CAPS) buffer solution, and thus embodiment 3 is not restrictive of the present disclosure.

The crosslinking process and the deamidation process are each applicable to all aspects of the preferred embodiments of the disclosure and thus are not restricted to any embodiments.

In an embodiment of the present disclosure, lubrication layer coating method of the biodegradable double-J stent 3 comprises the following.

Another clinical issue facing conventional double-J stents is about the need to reduce the static friction generated between the ureter and the double-J stent with a view to diminishing the discomfort caused to the patient by the insertion of the double-J stent into the ureter. In an embodiment of the present disclosure further provides a method to address the aforesaid issue, and the method involves coating a lubrication layer onto the surface of the biodegradable double-J stent to reduce the static friction generated between the ureter and the biodegradable double-J stent being inserted into the ureter. The method in an embodiment is described below. However, in a variant manufacturing process, hydrophilic modification is performed on the surface of the biodegradable double-J stent.

First, a 1% hyaluronic acid solution is provided to function as a hydrophilic material. Then, the hydrophilic material is coated, by spray coating, onto the surfaces of the main tube and the first retaining tube of the biodegradable double-J stent 3 to form a lubrication layer. The thickness of the lubrication layer is 50 μm and is adjustable within the range of 1 μm to 0.66 mm according to the manufacturing process or clinical needs or can even be changed to any other thickness values according to the manufacturing process or clinical needs as long as a lubrication effect conducive to the reduction of the static friction is achieved.

After the biodegradable double-J stent 3 has been coated with the lubrication layer, the biodegradable double-J stent 3 is placed in a room temperature environment to dry spontaneously. After the biodegradable double-J stent 3 has dried, the biodegradable double-J stent 3 is removed from the core to undergo a subsequent contact angle test.

In an embodiment of the present disclosure, the lubrication layer is coated on the main tube and the first retaining tube. However, in a variant embodiment, the lubrication layer is coated on the main tube, the first retaining tube, and the second retaining tube, i.e., coated fully on the biodegradable double-J stent 3. Therefore, this embodiment is not restrictive of the present disclosure.

In an embodiment of the present disclosure, hyaluronic acid functions as a hydrophilic material. However, in a variant manufacturing process, other biocompatible synthetic and natural hydrophilic polymers, such as synthetic hydrophilic polymer (for example, polyvinyl alcohol, polyethylene glycol, polyacrylic acid, silicone, polyethylene oxide), natural polysaccharide (for example, chitosan, alginate, agarose, starch, cellulose), natural protein (for example, collagen or gelatin), or a mixture or combination of the aforesaid materials, to function as a hydrophilic material. Therefore, the present disclosure is not restrictive thereto.

The lubrication layer can be applied to all aspects of the preferred embodiments of the disclosure and thus is not restricted thereto.

In an embodiment of the present disclosure a contact angle test for the biodegradable double-J stent 3 comprises the following.

Figure 6:
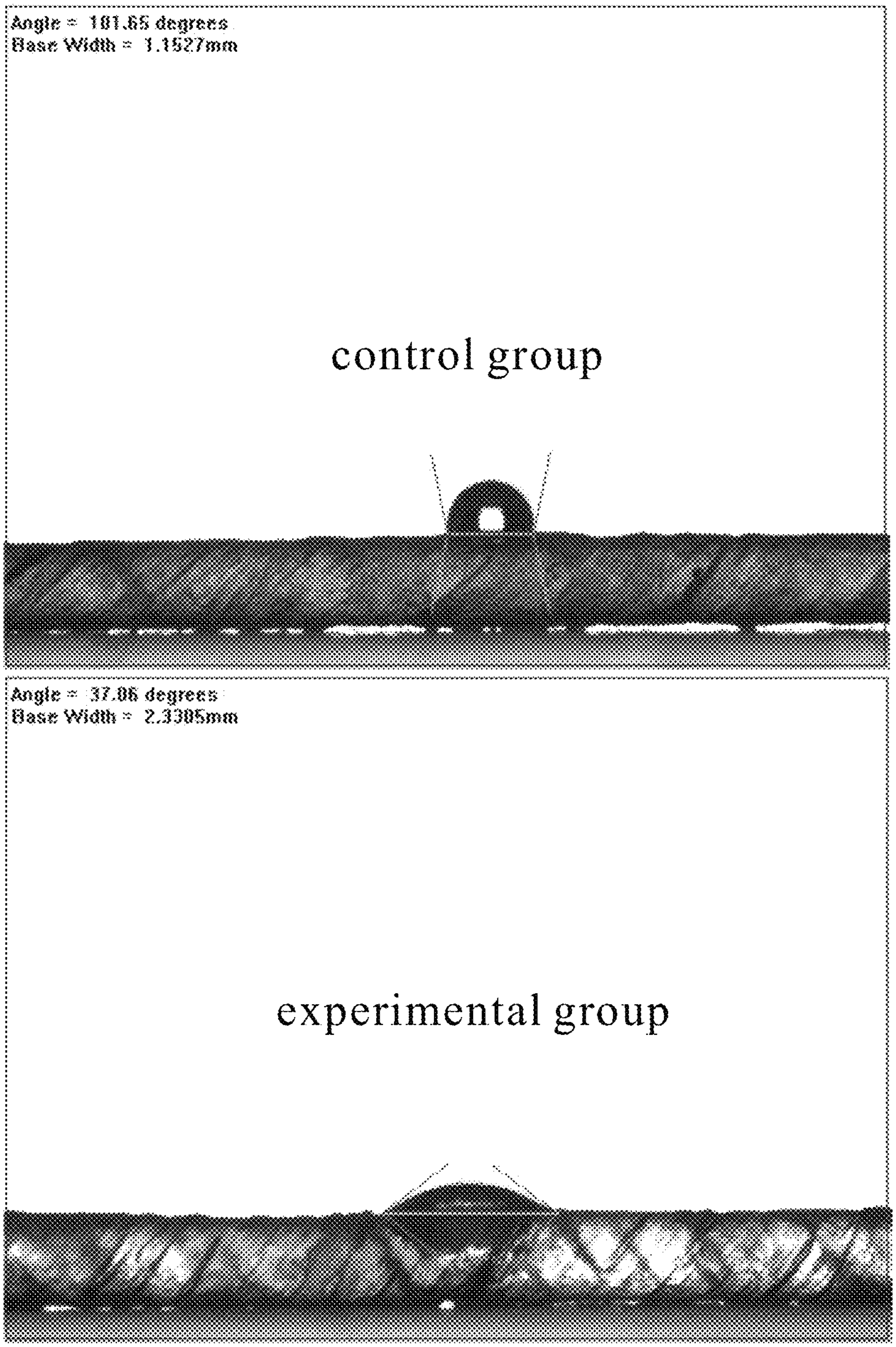
FIG. 6 shows a contact angle test result about the biodegradable double-J stent according to an embodiment of the present disclosure.

First, the biodegradable double-J stent 3, not coated with the lubrication layer, is provided to function as a control group, and the biodegradable double-J stent 3 coated with the lubrication layer is provided to function as an experimental group. Then, water droplets (around 0.5 μl) are dropped onto tube surfaces. Pictures are taken every second of the control group and the experimental group from the point in time when the water droplets (around 0.5 μl) adsorb on the tube surfaces, whereas at the $60^{th}$ second the contact angle between each water droplet and the adsorbing surface of the control group and the experimental group is measured, thereby finishing one instance of the contact angle test. The contact angle test is performed repeatedly three times to obtain the average contact angle and compare the control group and the experimental group in terms of the average contact angle. The smaller the contact angle is, the better the lubrication is. The test result is shown in FIG. 6. FIG. 6 shows the images taken of the experimental group and the control group at the $60^{th}$ second when the water droplets adsorb on the tube surface, and reveals that the contact angle (37.06 degrees) of the experimental group is around 40 degrees less than the contact angle (101.65 degrees) of the control group, indicating that the experimental group (the biodegradable double-J stent 3 coated with the lubrication layer) exhibits better lubrication effect than the control group (the biodegradable double-J stent 3 not coated with the lubrication layer) and thus reduces the static friction generated between the ureter and the double-J stent being inserted into the ureter.

In an embodiment of the present disclosure a contrast agent and lubrication combo layer coating method for the biodegradable double-J stent 3 comprises the following.

An embodiment of the present disclosure further provides a contrast agent and lubrication combo layer coating method effective in combining the advantage of a hydrophilic layer and the advantage of a subsequently formed contrast agent layer. The method of coating a contrast agent and lubrication combo layer on the surface of the biodegradable double-J stent 3 is described below.

First, a hyaluronic acid solution/bismuth oxychloride is provided to function as a material of which a contrast agent and lubrication combo layer is made. The hyaluronic acid solution functions as a hydrophilic material. The bismuth oxychloride functions as a radiopaque material. The required proportion of the hyaluronic acid solution/bismuth oxychloride solution is achieved as follows: 1 g of the bismuth oxychloride is suspended in the 1% hyaluronic acid solution. Then, the hydrophilic material is coated, by spray coating, onto the surfaces of the main tube and the first retaining tube of the biodegradable double-J stent 3 to form a contrast agent and lubrication combo layer. The thickness of the contrast agent and lubrication combo layer is 50 μm and is adjustable within the range of 1 μm to 0.66 mm according to the manufacturing process or clinical needs or can even be changed to any other thickness values as long as a lubrication effect conducive to the reducing static friction is achieved.

Figure 6A:
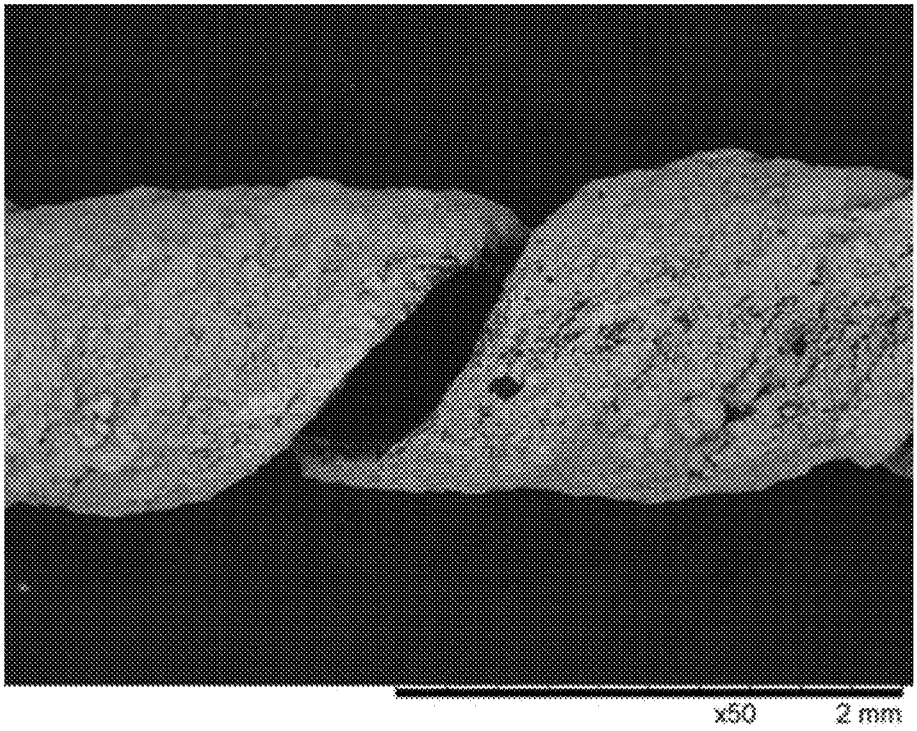
FIG. 6A is a partial enlarged view of a contrast agent and lubrication combo layer coated on the biodegradable double-J stent according to an embodiment of the present disclosure.

After the biodegradable double-J stent 3 has been coated with the contrast agent and lubrication combo layer, the biodegradable double-J stent 3 is placed in a room temperature environment to dry spontaneously. After the biodegradable double-J stent 3 has dried, the biodegradable double-J stent 3 is removed from the core. An image of the biodegradable double-J stent 3 coated with the contrast agent and lubrication combo layer is taken with an electron microscope (Hitachi TM1000) and shown in FIG. 6A.

In an embodiment of the present disclosure, the contrast agent and lubrication combo layer is applied on the main tube and the first retaining tube. However, in a variant embodiment, the contrast agent and lubrication combo layer is coated on the main tube, the first retaining tube, and the second retaining tube, i.e., coated fully on the biodegradable double-J stent 3. Therefore, embodiments are not restrictive of the present disclosure.

The contrast agent and lubrication combo layer can be applied to all aspects of the preferred embodiments of the present disclosure and thus is not restricted thereto.

In an embodiment of the present disclosure a method of manufacturing a biodegradable double-J stent comprises the following.

First, provide the extracellular matrix-derived material previously described to function as a biodegradable material. The extracellular matrix-derived material is plate-shaped. The extracellular matrix-derived material is cut to form a slender plate 15 mm in width and 1,500 mm in length.

Then, wind the extracellular matrix-derived material around itself to make 600 turns and thus form a screw rod. The number of turns is adjustable to meet manufacturing process needs. Next, a Teflon cord is prepared to function as a core. The diameter of the core is 0.99 mm and is adjustable within the range of 0.9 mm to 3.3 mm, depending on the requirements of the manufacturing process of the double-J stent. For example, the wider the channel in the double-J stent is, the greater the core diameter is, and vice versa. The lower end of the extracellular matrix-derived material shaped like a screw rod is fixed to the surface of the core, and the extracellular matrix-derived material winds around the core clockwise (or counterclockwise) and upward while tilting relative to the axis of the core by a tilt angle of 45° (or at least less than) 90° so as for the extracellular matrix-derived material shaped like a screw rod to take on a helical structure. At this point in time, the extracellular matrix-derived material shaped like a screw rod functions as a helical body of the helical structure. After winding completely around the core, the extracellular matrix-derived material shaped like a screw rod fully takes on the helical structure. The helical structure comprises a plurality of helical circles spaced apart from each other by a pitch of around 0.5 mm. The pitch of the helical structure is adjustable within the range of 0 mm to 2.5 mm, depending on the manufacturing process of and application needs for the double-J stent.

Figure 7:
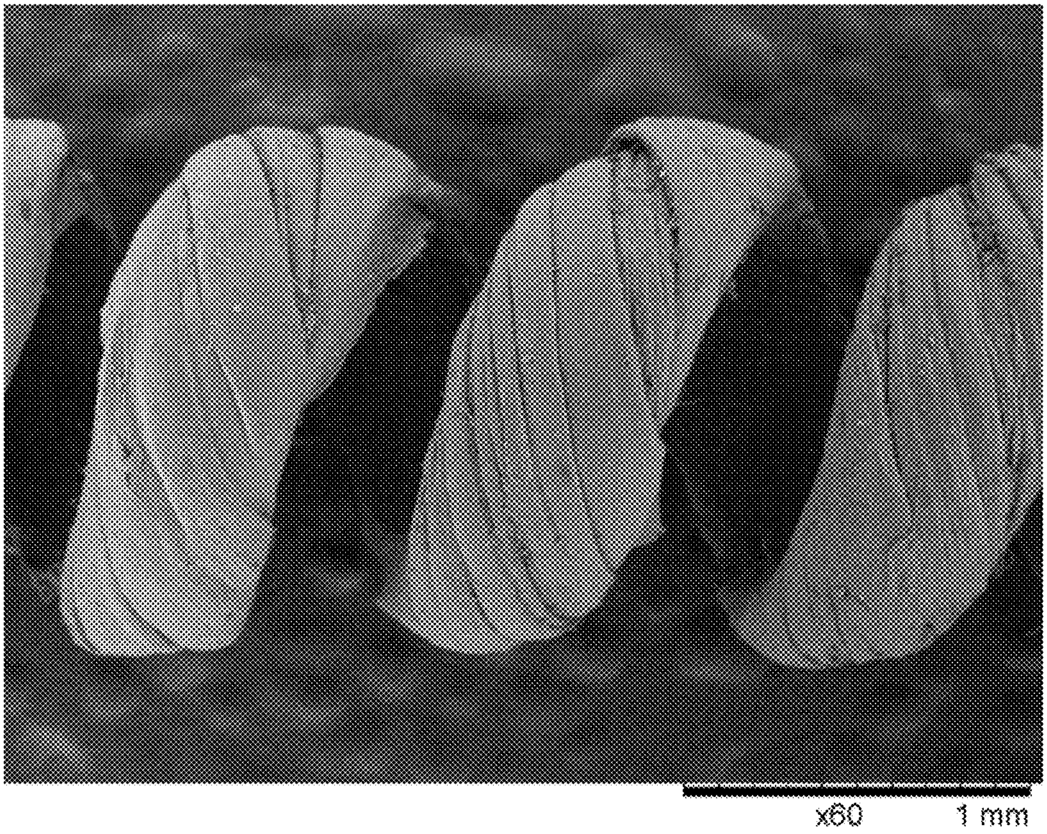
FIG. 7 is a partial enlarged view of a biodegradable double-J stent according to an embodiment of the present disclosure.

Finally, the two ends of the helical structure are bent into curl-shaped with the method previously described. Next, the bent helical structure undergoes a drying process with air at room temperature. After the bent helical structure has dried with air, it is removed from the core to obtain a biodegradable double-J stent 4. The overall shape of the biodegradable double-J stent 4 in an embodiment is substantially the same as that of the biodegradable double-J stents in the aforesaid embodiments. The image taken of the biodegradable double-J stent 4 with an electron microscope (Hitachi TM1000) is shown in FIG. 7. The helical circle structure in the helical structure of the biodegradable double-J stent 4 is a screw rod structure. In an embodiment of the present disclosure, a screw rod is made of the extracellular matrix-derived material, and then the screw rod is processed to form a helical structure, so as to further enhance the shape memory function and the mechanical strength of the biodegradable double-J stent 4.

In an embodiment of the present disclosure a compressive strength test for the biodegradable double-J stent 4 comprises the following.

First, provide the biodegradable double-J stent 4 and cut the biodegradable double-J stent 4 to form samples of experimental group 1 which are 3 cm in length. The biodegradable double-J stent 4 coated with a lubrication layer (illustrated by the coating process flow in the contact angle test of the biodegradable double-J stent 4, as described later) is provided. The biodegradable double-J stent 4 coated with the lubrication layer is cut to form samples of experimental group 2 which are 3 cm in length. After that, the biodegradable double-J stent 4 coated with a contrast agent and lubrication combo layer (illustrated by the coating process flow of the contrast agent and lubrication combo layer coating method of the biodegradable double-J stent 3, as described before) is provided. The biodegradable double-J stent 4 coated with the contrast agent and lubrication combo layer is cut to form samples of experimental group 3 which are 3 cm in length.

Then, an electronic tensile-testing machine is provided, and the distance between a pressing jig and a sample platform of the electronic tensile-testing machine is adjusted to 4 mm according to the outer diameter of samples of experimental groups 1-3.

Next, the compressive strength test is conducted with the electronic tensile-testing machine, using a load cell of 50 kg, a test speed (adjustable) of 10±0.5 mm/minute, a force tolerance of ±30 kg, and a deformation tolerance of ±1 mm. The maximum force of the initial compressive strength of the samples of experimental groups 1-3 is measured and recorded according to the aforesaid criteria. After the initial maximum compressive strength of the samples of experimental groups 1-3 has been measured, the samples of experimental groups 1-3 are soaked in normal saline at 37±3° C. for 10 minutes. Upon completion of the soaking step, the compressive strength test is carried out again, and the post-soaking maximum compressive strength of the samples of experimental groups 1-3 is recorded.

Upon completion of the compressive strength test of the samples of experimental groups 1-3, the double-J stent (stents purchased from Bioteq) of the control group is provided to become the samples of the control group. Next, according to the process flow, the compressive strength test is conducted on the samples of the control group once again. Finally, the samples of experimental groups 1-3 are compared with the samples of the control group in terms of the initial maximum compressive strength and post-soaking maximum compressive strength to evaluate their initial compressive strength and post-soaking compressive strength.

Figure 8:
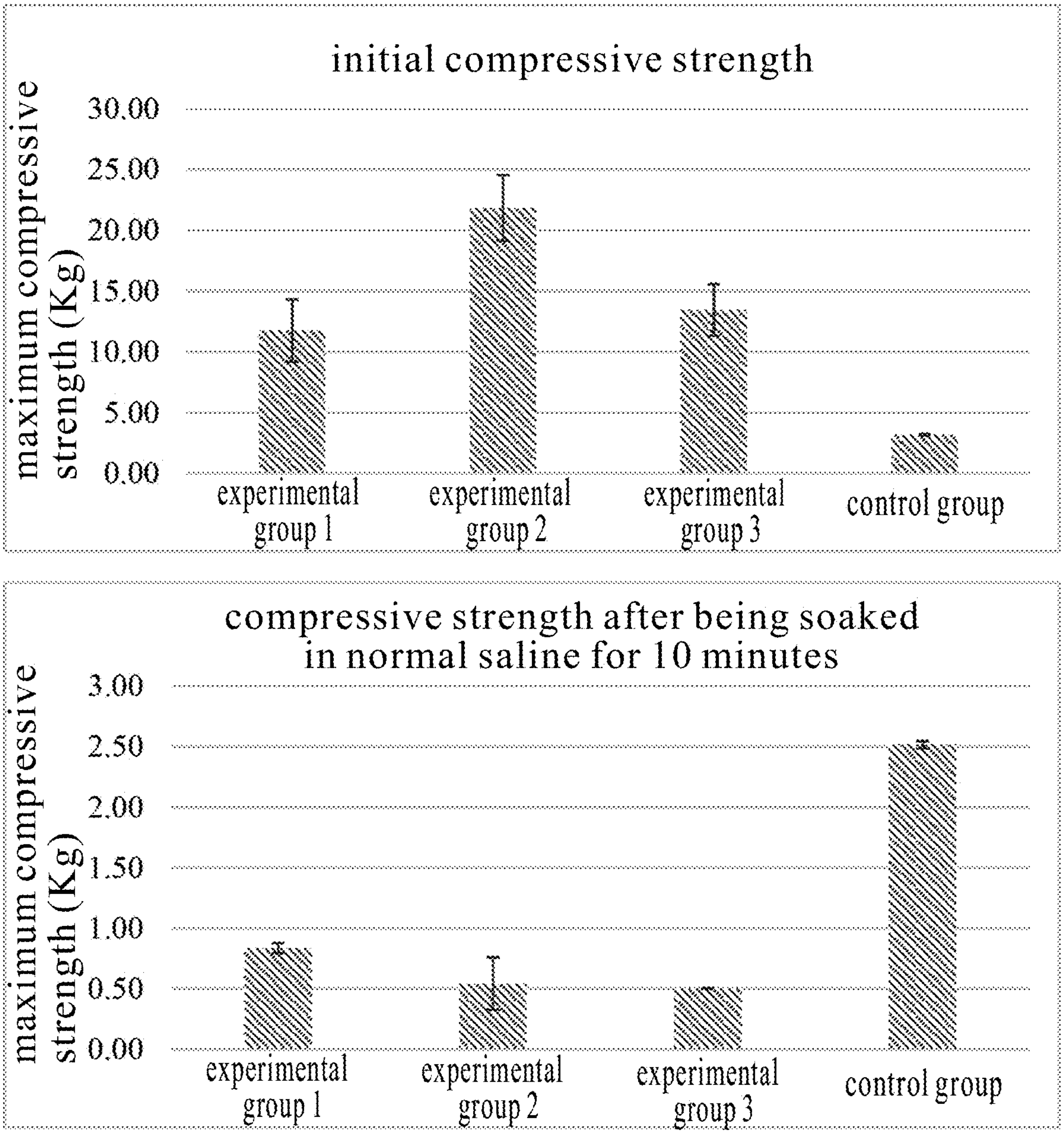
FIG. 8 shows a compressive strength test result about the biodegradable double-J stent according to an embodiment of the present disclosure.

The compressive strength test result shown in FIG. 8 reveals the following: regarding the initial compressive strength performance, experimental group 1 has a maximum compressive strength of 11.76 Kgf, experimental group 2 has a maximum compressive strength of 21.85 Kgf, experimental group 3 has a maximum compressive strength of 13.45 Kgf, and the control group of the double-J stent has a maximum compressive strength of 3.18 Kgf. As suggested by the aforesaid initial compressive strength data, screw rod-helical tube braided structures formed from experimental groups 1-3 with the braiding method are effective in further enhancing their mechanical strength. Regarding the post-soaking compressive strength performance, the control group of the double-J stent has a maximum compressive strength of 2.52 Kgf, experimental group 1 has a maximum compressive strength of 0.84 Kgf, experimental group 2 has a maximum compressive strength of 0.54 Kgf, and experimental group 3 has a maximum compressive strength of 0.5 Kgf. As suggested by the aforesaid post-soaking compressive strength data, after being soaked in normal saline for 10 minutes, the double-J stents of experimental groups 1-3 demonstrate radial compressive capability (i.e., the compressive strength) that has decreased by 93~97% and still maintain low radial compressive capability required for human body tissues. Furthermore, the biodegradable double-J stent 4 is soaked in normal saline to reduce its radial compressive capability. This reduction not only allows the physician in easily placing the biodegradable double-J stent 4 in the patient's ureter, but also diminishes the patient's sensation of a foreign body, thereby significantly reducing the patient's discomfort.

In an embodiment of the present disclosure a kink test for the biodegradable double-J stent 4 comprises the following.

First, provide the biodegradable double-J stent 4 and the control group of the double-J stent. Furthermore, two metallic posts each with a diameter of 8 mm are fixed to a wall, and the middle segments of the biodegradable double-J stent 4 and the control group of the double-J stent are rested on the metallic posts and tightly fitted to the semicircles of the metallic posts, respectively. Then, the kink test is finished by observing whether the biodegradable double-J stent 4 and the control group of the double-J stent bend at parts thereof surrounding the metallic posts.

Figure 9:
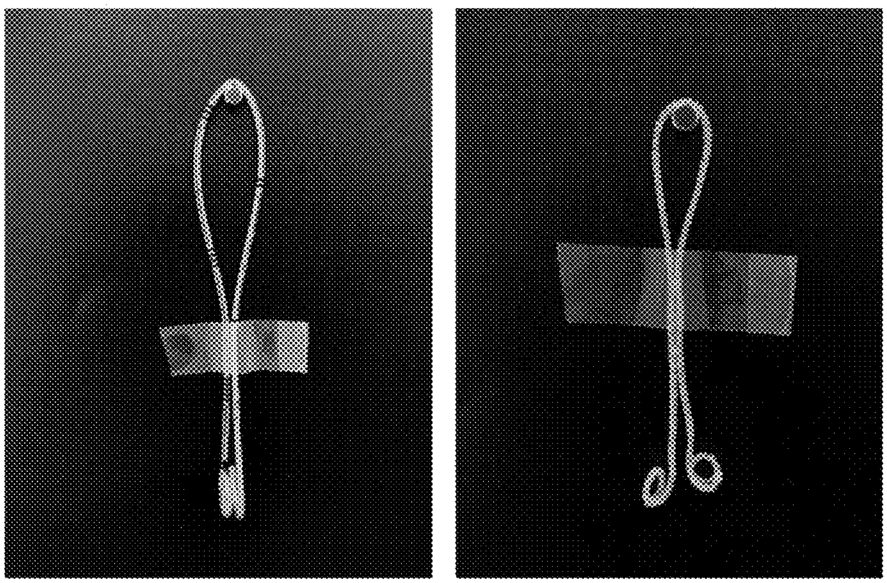
FIG. 9 shows a kink test result about the biodegradable double-J stent according to an embodiment of the present disclosure.

The test result, as shown in FIG. 9, indicates that the middle segment (i.e., the main tube) of the biodegradable double-J stent 4 (on the right in FIG. 9) curves (i.e., the post-surrounding part of the double-J stent is an arc) instead of bends (i.e., the post-surrounding part of the double-J stent is a kink), but the middle segment of the control group of the double-J stent (on the left in FIG. 9) bends, increasing the likelihood of blocking the space of the middle segment.

Then, the biodegradable double-J stent 4 is tested further by fixing a metallic post with a diameter of 2 mm to a wall and determining, in accordance with the process flow, whether the post-surrounding part of the biodegradable double-J stent 4 bends.

Figure 10:
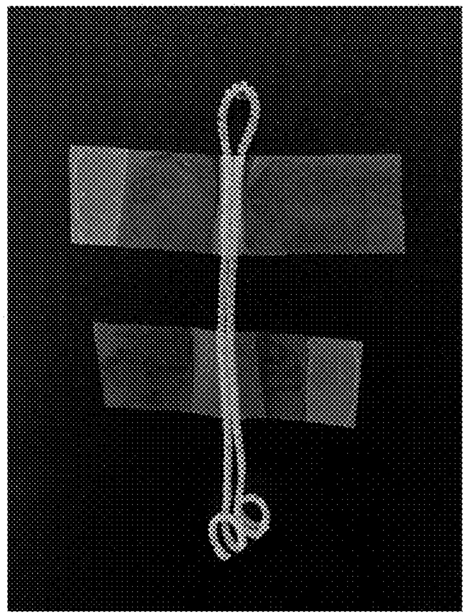
FIG. 10 shows another kink test result about the biodegradable double-J stent according to an embodiment of the present disclosure.

The test result shown in FIG. 10 is as follows. Although the metallic post with a diameter of 2 mm causes the biodegradable double-J stent 4 to curve, the middle segment (i.e., the main tube) of the biodegradable double-J stent 4 does not bend.

As suggested by the aforesaid test results, the screw rod-helical tube braided structure, which is formed to constitute the biodegradable double-J stent 4 using the previously described braiding method, is effective in preventing bend-induced obstruction of the lumen of the urinary tract. Once the biodegradable double-J stent 4 is placed in the patient's body, it thereby averts failure of the urine within the lumen to exit or flow normally.

In an embodiment of the present disclosure a shape memory test of the biodegradable double-J stent 4 comprises the following.

First, provide the biodegradable double-J stent 4. Furthermore, prepare a normal saline solution, add the normal saline solution into a Petri dish with a diameter of 10 cm at room temperature, and keep a liquid level of around 0.5 cm high in the Petri dish. Then, the second retaining tube is cut off from the biodegradable double-J stent 4 and stretched with a universal testing machine such that the stretched length of the second retaining tube thus stretched is 200% that of the original length of the second retaining tube. Finally, the second retaining tube thus stretched is placed in the normal saline solution in the Petri dish and continuously observed to determine whether the second retaining tube thus stretched can restore its initial curled state.

Figure 11:
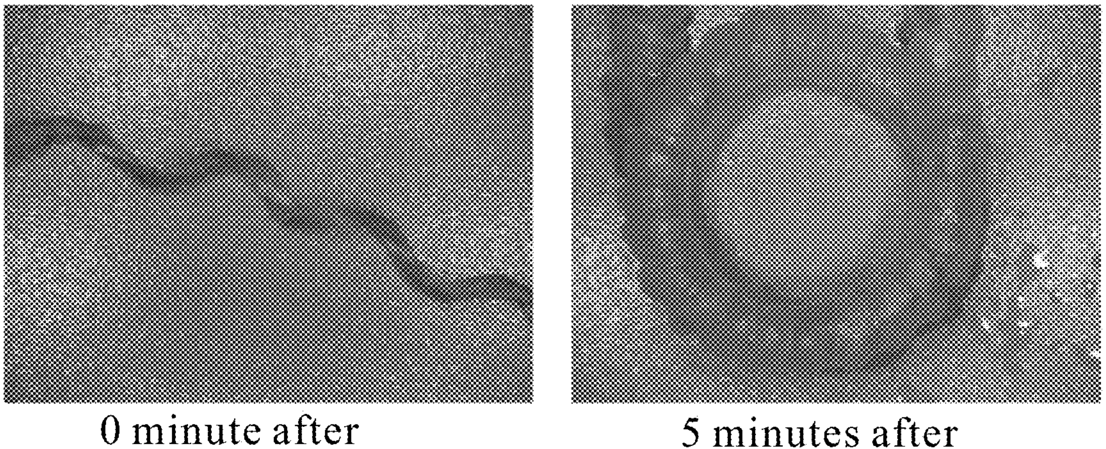
FIG. 11 shows a shape memory test result about the biodegradable double-J stent according to an embodiment of the present disclosure.

The test result, as shown in FIG. 11, indicates that, after being placed in the normal saline solution for 5 minutes, the second retaining tube thus stretched restores its initial curled state.

As suggested by the aforesaid test results, the screw rod-helical tube braided structure, formed to embody the biodegradable double-J stent 4 with the braiding method, effectively maintains a deformation-resistant shape memory function. The structure preventing the biodegradable double-J stent 4 detaching from the urinary bladder and the affected renal pelvis, a common issue arising in lengthy surgery due to reduced curling.

In an embodiment of the present disclosure a contact angle test for the biodegradable double-J stent 4 comprises the following.

Figure 12:
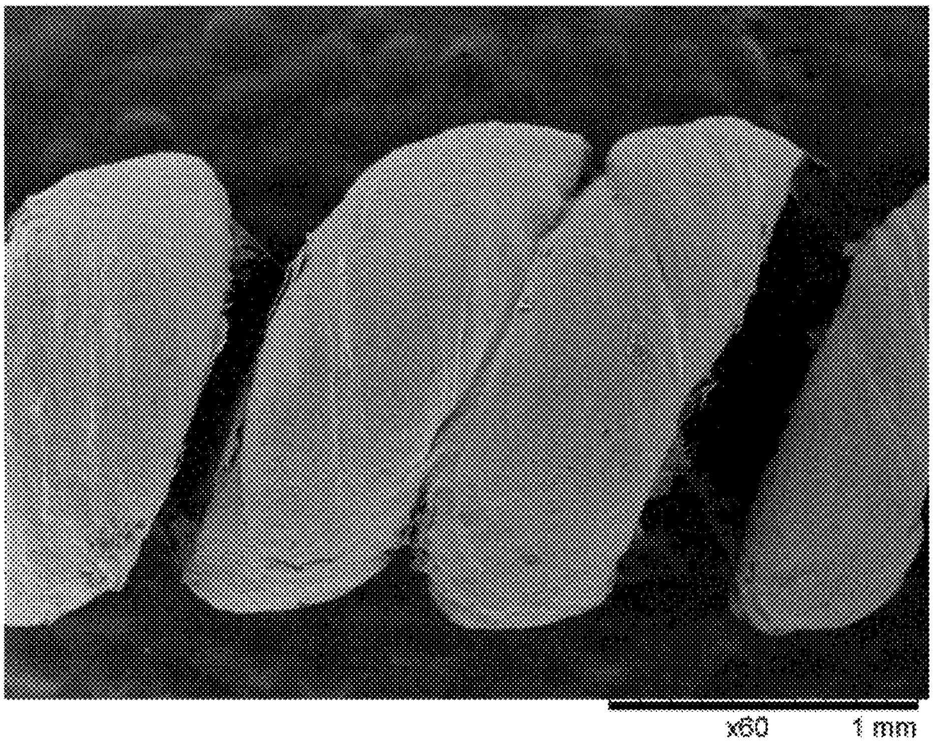
FIG. 12 is a partial enlarged view of the biodegradable double-J stent which has undergone hydrophilic coat treatment according to an embodiment of the present disclosure.

To test and determine whether the biodegradable double-J stent 4 embodied in the form of the screw rod-helical tube braided structure still has a lubrication effect after being coated with the lubrication layer, it is feasible to coat the lubrication layer on the surface of the biodegradable double-J stent 4 with the lubrication layer coating method previously described, conduct a contact angle test on the biodegradable double-J stent 4 in accordance with the contact angle test process flow previously described, use the biodegradable double-J stent 4 coated with the lubrication layer as an experimental group, and use the biodegradable double-J stent 4 not coated with the lubrication layer as the control group. The image of the biodegradable double-J stent 4 coated with the lubrication layer, captured by an electron microscope (Hitachi TM1000), is shown in FIG. 12, showing that its surface is smooth.

Figure 13:
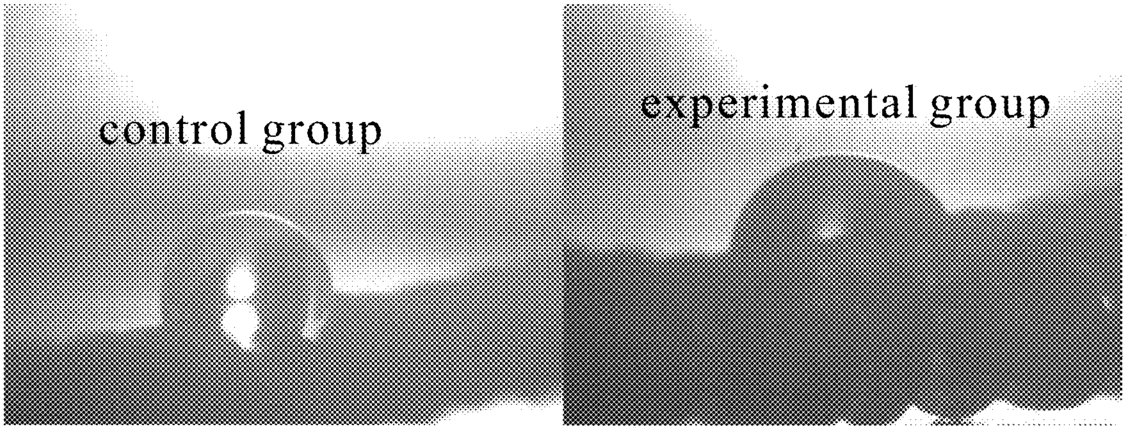
FIG. 13 shows a contact angle test result about the biodegradable double-J stent according to an embodiment of the present disclosure.

The test result is shown in FIG. 13. FIG. 13 shows images taken of the experimental group and the control group at the $60^{th}$ second after water droplets have adsorbed on the tube surfaces. As indicate by the images, the contact angle of the experimental group is smaller than the contact angle of the control group, and the experimental group (the biodegradable double-J stent 4 coated with the lubrication layer) surpasses the control group (the biodegradable double-J stent 4 not coated with the lubrication layer) in the lubrication effect, reducing the static friction generated between the ureter and the double-J stent being inserted into the ureter and thereby effectively reducing the discomfort otherwise resulting from the static friction.

In an embodiment of the present disclosure a contrast agent coating method for the biodegradable double-J stent 4 comprises the following.

Yet another clinical issue facing conventional double-J stents is about the need to improve the sharpness of X-ray images taken of double-J stents in a patient's body during a follow-up consultation intended to locate and observe the double-J stents. In view of this, an embodiment further provides a method for addressing the aforesaid issue by coating a contrast agent layer on the surface of the biodegradable double-J stent to allow the biodegradable double-J stent to be shown clearly in X-ray images. A method of coating contrast agent on the surface of the biodegradable double-J stent 3 is described below.

First, polycaprolactone/barium sulfate is prepared to function as a radiopaque material, and the required proportion of polycaprolactone/barium sulfate is achieved as follows: 0.5 g of barium sulfate and 0.5 g of polycaprolactone are dissolved in 1% dichloromethane, and the radiopaque material is coated, by spray coating, onto the surfaces of the main tube and the first retaining tube of the biodegradable double-J stent 4 to form a contrast agent layer. The thickness of the contrast agent layer is 20 μm and is adjustable within the range of 5 μm to 0.66 mm according to the manufacturing process or clinical needs or can even be changed to any other thickness values according to the manufacturing process or clinical needs as long as clear imaging is attained.

Figure 14:
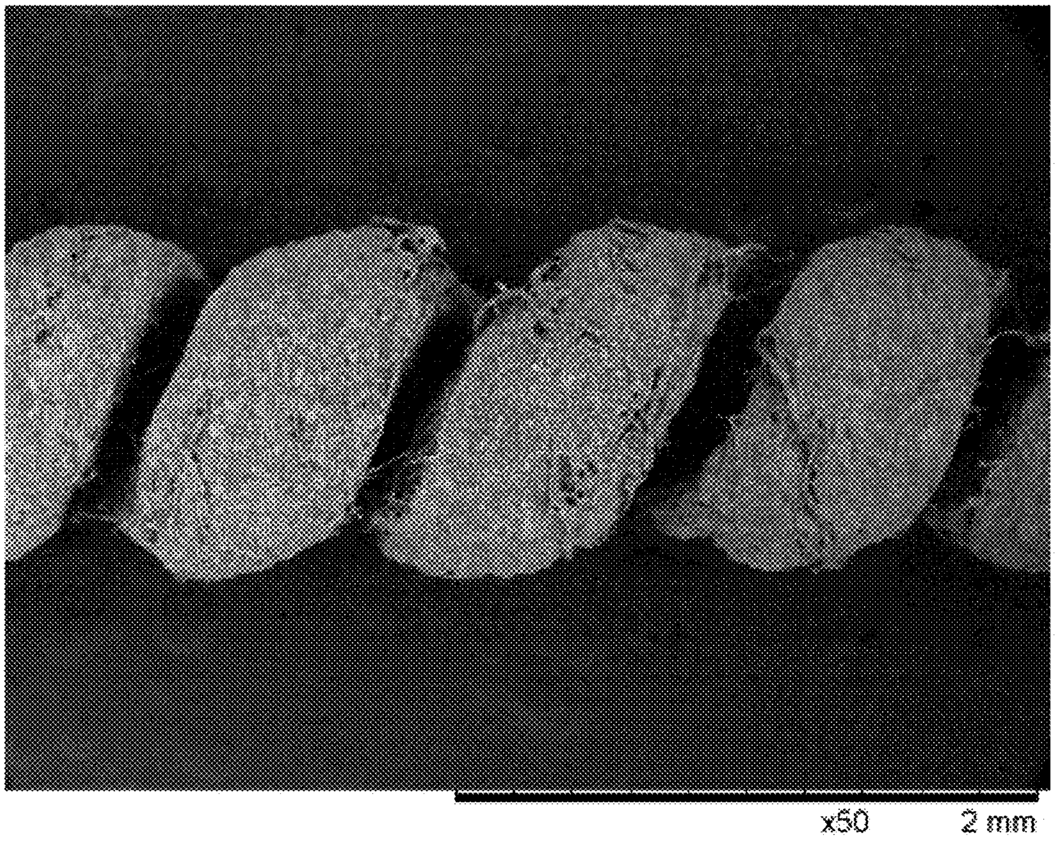
FIG. 14 is a partial enlarged view of the biodegradable double-J stent which has been coated with a contrast agent according to an embodiment of the present disclosure.

After the biodegradable double-J stent 4 has been coated with the contrast agent layer, the biodegradable double-J stent 4 is placed in a room temperature environment to dry spontaneously. After the biodegradable double-J stent 4 has dried, the biodegradable double-J stent 4 can undergo a subsequent X-ray imaging test. An image of the biodegradable double-J stent 4 coated with the contrast agent layer is taken with an electron microscope (Hitachi TM1000) and shown in FIG. 14, showing the roughness of the surface of the biodegradable double-J stent 4.

In an embodiment of the present disclosure, the contrast agent layer is coated on the main tube, the first retaining tube, and the second retaining tube, i.e., coated fully on the biodegradable double-J stent 4. However, in a variant embodiment, the contrast agent layer is coated on the first retaining tube and/or the second retaining tube. Therefore, the present disclosure is not restricted thereto.

In an embodiment of the present disclosure, polycaprolactone/barium sulfate functions as a radiopaque material. However, a variant manufacturing process uses other known, existing radiopaque materials, such as metals, including barium, bismuth, iodine, gold, silver, copper, iron, aluminum, lithium, zinc, and platinum, their salts or polymers, or a mixture or combination of the aforesaid materials. Therefore, the present disclosure is not restricted thereto.

The aforesaid contrast agent layer can be applied to all aspects of the preferred embodiments of the disclosure and thus is not restricted.

In an embodiment of the present disclosure an X-ray imaging test for the biodegradable double-J stent 4 comprises the following.

First, the biodegradable double-J stent 4 not coated with the contrast agent layer is provided to function as experimental group 1, the biodegradable double-J stent 4 with the retaining tubes (at its two ends) coated with the contrast agent layer is provided to function as experimental group 2, and the biodegradable double-J stent 4 entirely coated with the contrast agent layer is provided to function as experimental group 3.

Next, X-ray images are taken of experimental groups 1-3 in a non-hidden environment, and then X-ray images are taken of experimental groups 1-3 hidden by a body mimic (using chicken breast as the body mimic). The X-ray is generated from a C-arm perspective X-ray generator. According to the default settings of the X-ray generator, the X-ray generator is placed at a point around 100 cm away from experimental groups 1-3 to take X-ray images at room temperature.

Figure 15:
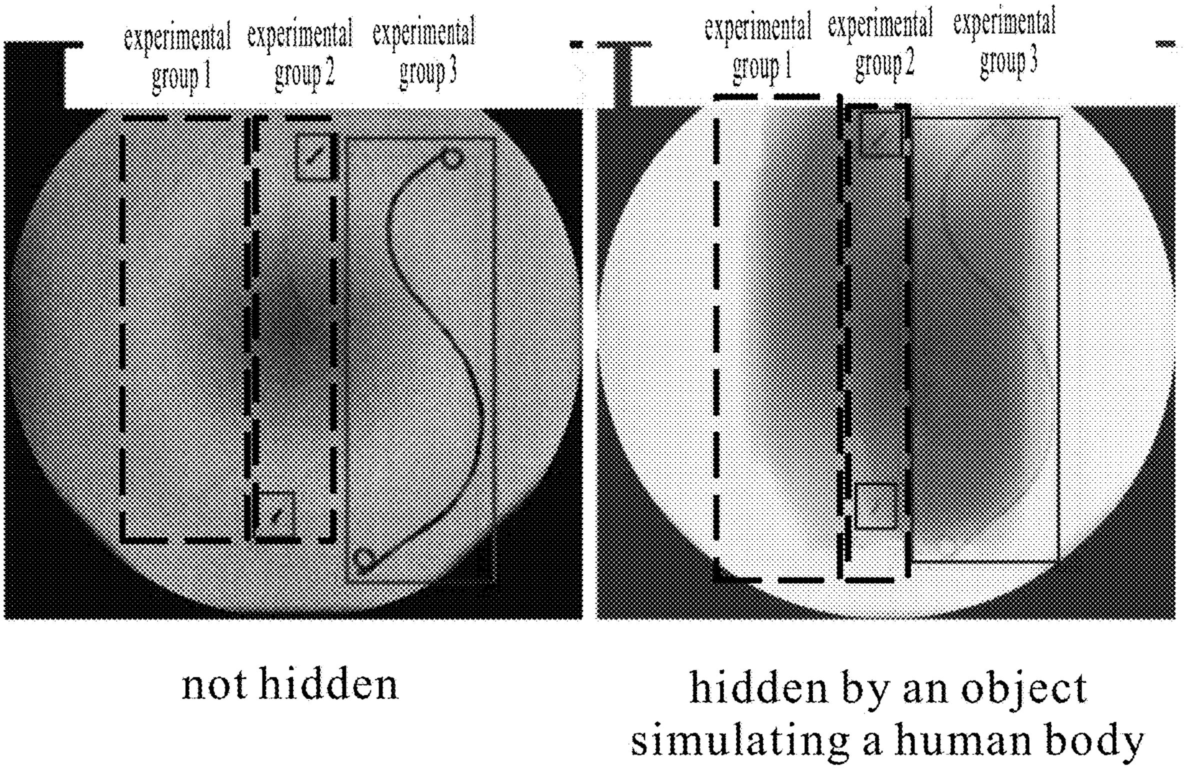
FIG. 15 shows an X-ray imaging test result about the biodegradable double-J stent which has been coated with a contrast agent according to an embodiment of the present disclosure.

The aforesaid X-ray imaging test result shown in FIG. 15 reveals the following: X-ray images of experimental group 1 are blurred, whether experimental group 1 is in a non-hidden environment or is hidden by the body mimic; X-ray images of experimental group 2 clearly show the retaining tubes at the two ends of the biodegradable double-J stent 4, whether experimental group 2 is in a non-hidden environment or is hidden by the body mimic; and X-ray images of experimental group 3 clearly show the entire outline of the biodegradable double-J stent 4, whether experimental group 3 is in a non-hidden environment or is hidden by the body mimic.

The aforesaid test result reveals that the aforesaid contrast agent layer enables the biodegradable double-J stent to be clearly shown in X-ray images and thus allows a physician to precisely locate the double-J stent in the patient's body.

Therefore, the present disclosure provides a biodegradable double-J stent entirely made of a biocompatible, biodegradable material to allow the biodegradable double-J stent to degrade inside the patient's body spontaneously, precluding a ureteral obstruction which might otherwise occur with conventional double-J stents not removed in a timely manner. In addition, braided structures, such as the helical tube and the screw rod, further boost the mechanical strength, structural strength, and shape memory function of the biodegradable double-J stent. Moreover, the degradation rate of every part of the biodegradable double-J stent is adjustable with a crosslinking process and a deamidation process according to clinical needs. In addition, the biodegradable double-J stent is coated with a lubrication layer for reducing the static friction generated between the ureter and the double-J stent being inserted into the ureter and coated with a contrast agent layer, rendering the biodegradable double-J stent in X-ray images clear.

The present disclosure is disclosed above by preferred embodiments. However, persons skilled in the art understand that the embodiments are illustrative of the present disclosure only and shall not be interpreted to restrict the scope of the present disclosure. It is noteworthy that all changes and replacements made to the embodiments and are equivalent thereto shall be deemed falling within the scope of the present disclosure. Accordingly, the legal protection for the present disclosure should be defined by the appended claims.

What is claimed is:

1. A biodegradable double-J stent, comprising:

a main tube made of a biodegradable material with biocompatibility and having a first end portion and a second end portion opposing the first end portion;

a first retaining tube made of the biodegradable material, curled, and connected to the first end portion of the main tube; and a second retaining tube made of the biodegradable material, curled, and connected to the second end portion of the main tube;

wherein the biodegradable material consists essentially of collagen derived from an organism;

wherein the main tube comprises a helical structure formed by a screw rod winding along a longitudinal axis, the biodegradable material is formed as a single slender plate, and the screw rod is formed by winding the single slender plate around itself.

2. The biodegradable double-J stent of claim 1, wherein the main tube and/or the first retaining tube features a first degradation rate, and the second retaining tube features a second degradation rate, with the first and second degradation rates being different from each other.

3. The biodegradable double-J stent of claim 2, wherein the first degradation rate is faster than the second degradation rate.

4. The biodegradable double-J stent of claim 2, wherein the first degradation rate is slower than the second degradation rate.

5. The biodegradable double-J stent of claim 1, further comprising a lubrication layer made of a biocompatible, hydrophilic material or having a surface hydrophilically modified, wherein the lubrication layer is coated on:

(i) the main tube, the first retaining tube, and the second retaining tube; or (ii) the main tube and the first retaining tube.

6. The biodegradable double-J stent of claim 5, wherein the lubrication layer is 1 μm to 0.66 mm in thickness.

7. The biodegradable double-J stent of claim 1, further comprising a contrast agent layer made of a biocompatible radiopaque material, wherein the contrast agent layer is coated on:

(i) the main tube, the first retaining tube, and the second retaining tube; or (ii) at least one of the first retaining tube and the second retaining tube.

8. The biodegradable double-J stent of claim 7, wherein the contrast agent layer is 1 μm to 0.66 mm in thickness.

9. The biodegradable double-J stent of claim 1, further comprising a contrast agent and lubrication combo layer made of a mixture of a biocompatible radiopaque material and a biocompatible, hydrophilic material, wherein the contrast agent and lubrication combo layer is coated on:

(i) the main tube, the first retaining tube, and the second retaining tube; or (ii) at least one of the first retaining tube and the second retaining tube.

10. The biodegradable double-J stent of claim 9, wherein the contrast agent and lubrication combo layer is 1 μm to 0.66 mm in thickness.

11. The biodegradable double-J stent of claim 1, wherein the main tube, the first retaining tube, and the second retaining tube are integrally formed.

12. The biodegradable double-J stent of claim 11, wherein the helical structure comprises a plurality of helical circles spaced apart from each other by a pitch of 0 mm to 2.5 mm.

13. The biodegradable double-J stent of claim 1, wherein the main tube has an outer diameter of 0.33 mm to 3.33 mm.

14. A method of manufacturing a biodegradable double-J stent, comprising the steps of:

(a) providing a tube made of a biodegradable material with biocompatibility, wherein the biodegradable material consists essentially of collagen derived from an organism, and the biodegradable material is formed as a single slender plate; and (b) bending two ends of the tube to render the two ends curl-shaped and keeping a middle segment between the two ends straight, wherein the two curl-shaped ends define a first retaining tube and a second retaining tube, respectively, and the middle segment defines a main tube, wherein the main tube comprises a helical structure formed by a screw rod winding along a longitudinal axis on a core, and the screw rod is formed by winding the single slender plate around itself.

15. The method of claim 14, wherein the core is made of Teflon or stainless steel.

16. The method of claim 15, wherein the core has a diameter ranging from 0.9 mm to 3.3 mm.

17. The method of claim 14, wherein the main tube and the first retaining tube undergo a crosslinking process, and the main tube and/or the first retaining tube has a higher degradation rate than the second retaining tube or a lower degradation rate than the second retaining tube because of the crosslinking process.

18. The method of claim 17, wherein the crosslinking process is carried out with a crosslinking agent being one selected from the group consisting of an aldehyde-based crosslinking agent, isocyanate-based crosslinking agent, acyl azide-based crosslinking agent, epoxide-based crosslinking agent, quinone-based crosslinking agent, carbohydrate-based crosslinking agent, polyphenol-based crosslinking agent, and iridoid glycoside-based crosslinking agent.

19. The method of claim 18, wherein the crosslinking agent is carbodiimide/N-hydroxysuccinimide crosslinking agent.

20. The method of claim 14, wherein the second retaining tube undergoes a deamidation process.

* * * * *